(12) United States Patent
Rao (10) Patent No.: US 8,264,690 B2
(45) Date of Patent: Sep. 11, 2012

(54) METHOD AND APPARATUS FOR THE DETECTION OF TRACE GAS SPECIES USING MULTIPLE LINE INTEGRATED ABSORPTION SPECTROSCOPY

(75) Inventor: Gottipaty Rao, West Hempstead, NY (US)

(73) Assignee: Adelphi University, Garden City, NY (US)

( * ) Notice: Subject to any disclaimer, the term of this patent is extended or adjusted under 35 U.S.C. 154(b) by 0 days.

(21) Appl. No.: 12/878,553

(22) Filed: Sep. 9, 2010

(65) Prior Publication Data

US 2012/0062895 A1    Mar. 15, 2012

(51) Int. Cl.
*G01N 21/00* (2006.01)
(52) U.S. Cl. ....................................... 356/437
(58) Field of Classification Search ........................ None
See application file for complete search history.

(56) References Cited

U.S. PATENT DOCUMENTS

| | | | | |
|---|---|---|---|---|
| 4,434,490 A | * | 2/1984 | Kavaya et al. | 372/20 |
| 7,004,909 B1 | * | 2/2006 | Patel et al. | 73/23.3 |
| 7,102,751 B2 | * | 9/2006 | Harper | 356/437 |
| 2007/0064748 A1 | * | 3/2007 | Mirov et al. | 372/20 |
| 2007/0229834 A1 | * | 10/2007 | Patel et al. | 356/432 |

* cited by examiner

*Primary Examiner* — Gregory J Toatley
*Assistant Examiner* — Juan D Valentin
(74) *Attorney, Agent, or Firm* — Leason Ellis LLP.

(57) ABSTRACT

An apparatus and method are used to enhance the sensitivity of a spectrometer (sensor) for trace gas species detection by employing an external cavity continuously tunable CW quantum cascade laser and integrating the absorption spectra across multiple lines of the species. With this method the absorption spectra of $NO_2$ is continuously recorded across the R-branch from 1628.8 $cm^{-1}$ to 1634.5 $cm^{-1}$. By integrating the resulting spectra, the detection sensitivity for $NO_2$ is improved by a factor of 15 compared to the sensitivity achieved using single line laser absorption spectroscopy with the same apparatus. This procedure offers much shorter data acquisition times for the real-time monitoring of trace gas species compared with adding repeated scans of the spectra to improve the signal-to-noise ratio.

31 Claims, 7 Drawing Sheets

METHOD AND APPARATUS FOR THE DETECTION OF TRACE GAS SPECIES USING MULTIPLE LINE INTEGRATED ABSORPTION SPECTROSCOPY

BACKGROUND OF THE INVENTION

The present invention relates to the detection of trace amounts of gas species and, more particularly to laser-based systems for trace detection of nitrogen dioxide.

The precise monitoring of trace gases has applications in a wide range of fields, including the detection of environmental pollutants, tracking of contaminants in closed environmental systems, medical diagnostics, defense, and homeland security. In particular, real-time trace gas detection is important in environmental science (e.g., in atmospheric physics/chemistry concerning air quality control, for complying with Environmental Protection Agency (EPA) air quality regulations, safety monitoring, monitoring automobile emissions, as well as for the study of chemical reactions that environmental gases (such as $NO_2$) undergo particularly in the presence of solar radiation). See for example, United States Environmental Protection Agency, "National Air Quality Status and Trends Through 2007, EPA-454/R-08-006", United States Environmental Protection Agency, Washington D.C., (2008). In these applications the concentrations of pollutants typically range from parts per trillion ("ppt") to parts-per-million ("ppm") levels, and thus require techniques that are both highly sensitive and selective. Nitrogen oxides ($NO_x$) are some of the more damaging of these pollutants and impact the environment and public health in multiple ways. They play important roles in the formation of photochemical smog, the formation of tropospheric ozone and the formation of acid rain.

Laser-based techniques for monitoring environmental pollutants in the air have many advantages over chemical and other techniques because of their ability to provide real-time monitoring capabilities with greater sensitivity and selectivity. In particular, the advent of quantum cascade lasers in the mid-infrared region covering the 4-24 μm range has provided an attractive source for investigating the spectroscopy of trace gases in the atmosphere and for constructing portable gas sensors. See Kosterev el al., "Chemical Sensing with pulsed QC-DFB lasers operating at 6.6 μm" *Appl. Phys. B.* 75, 351-357 (2002). Quantum cascade lasers provide access to the fundamental rotational-vibrational transitions of molecular species, thus offering improved sensitivity of several orders of magnitude over near-infrared diode laser based techniques that employ the detection of the overtones of these transitions. See Tittel et al., "Recent Advances in Trace Gas Detection Using Quantum and Interband Cascade Lasers," *Rev. of Laser Eng.* 34, 275-282 (2006). Quantum cascade lasers have been used to detect several trace gasses (e.g., CO, $CO_2$, NO, $NH_3$, $CH_4$ and $N_2O$) with different spectroscopic techniques (e.g., laser absorption spectroscopy, Cavity Ringdown Spectroscopy, Integrated Cavity Output Spectroscopy) as described in the review articles by A. Kosterev e. al., "Application of quantum cascade lasers to trace gas analysis," Appl. Phys. B 90, 165-176 (2008); and R. F. Curl et al., "Quantum cascade lasers in chemical physics" Chem. Phys. Lett. 487, 1-18 (2010). By employing an external cavity arrangement, a quantum cascade laser offers a narrow linewidth ($\Delta\nu$~0.001 $cm^{-1}$), highly stable and reproducible tunable continuous wave ("CW") output, and a wide continuous tuning range; all of which are desirable for the study of complex spectra, as is the case in investigating trace gas components in the atmosphere. Examples of such prior studies include Wysocki et al., "Widely tunable mode-hop free external cavity quantum cascade laser for high resolution spectroscopic applications," *Appl. Phys.* B 81, 769-777 (2005); and Karpf & Rao, "Absorption and wavelength modulation spectroscopy of $NO_2$ using a tunable, external cavity continuous wave quantum cascade laser," *Appl. Opt.* 48, 408-413 (2009).

Laser Absorption Spectroscopy is based on recording the change in intensity of laser radiation as it passes through a region containing the sample of interest. As the laser is tuned across a transition, the transmitted laser intensity is a function of frequency $\nu$ given by Beer's law:

$$I(\nu) = I_0(\nu) e^{-\sigma(\nu)LN} \quad (1)$$

where $I_0$ is the incident laser intensity, L is the optical path length, $\sigma(\nu)$ is the absorption coefficient and N is the concentration of the absorbing species in molecules per unit volume. See P. Werle, "Review of recent advances in laser based gas monitors," *Spectrochimica Acta A* 54, 197-236 (1998). The absorbance of the species in the cell is defined by $a=\sigma(\nu)LN$, and the maximum value of the absorbance of a line corresponds to $a_{max}$.

The sensitivity of a spectrometer is often determined by taking the ratio of the amplitudes of the absorption line to that of the noise level. As a result, it is important to maintain the sample at a pressure that results in a narrow linewidth and large amplitude. Maintaining the sample at low pressure reduces collisional broadening. At high pressures, neighboring lines tend to overlap because of collisional broadening. For example, the full width at half maximum ("FWHM") of the strongest $NO_2$ transitions in the R-branch ($\nu$~1630 $cm^{-1}$) at atmospheric pressure are ~0.15 $cm^{-1}$, which is much greater than the separation between the individual lines. See Rothman et al., "The HITRAN 2004 molecular spectroscopic database", *J. Quant. Spectrosc. Radiat. Transfer* 96 139-204 (2005). It has been found that the optimal pressure for laser absorption techniques such as Tunable Diode Laser Absorption Spectroscopy (TDLAS) is in the 10-50 mbar range which provides the best balance between sensitivity and selectivity. See, J. M. Hollas, *High Resolution Spectroscopy, Second Edition*, (Wiley 1998). Standard techniques such as adding multiple scans may be used to enhance the signal-to-noise ratio.

Figure 1:
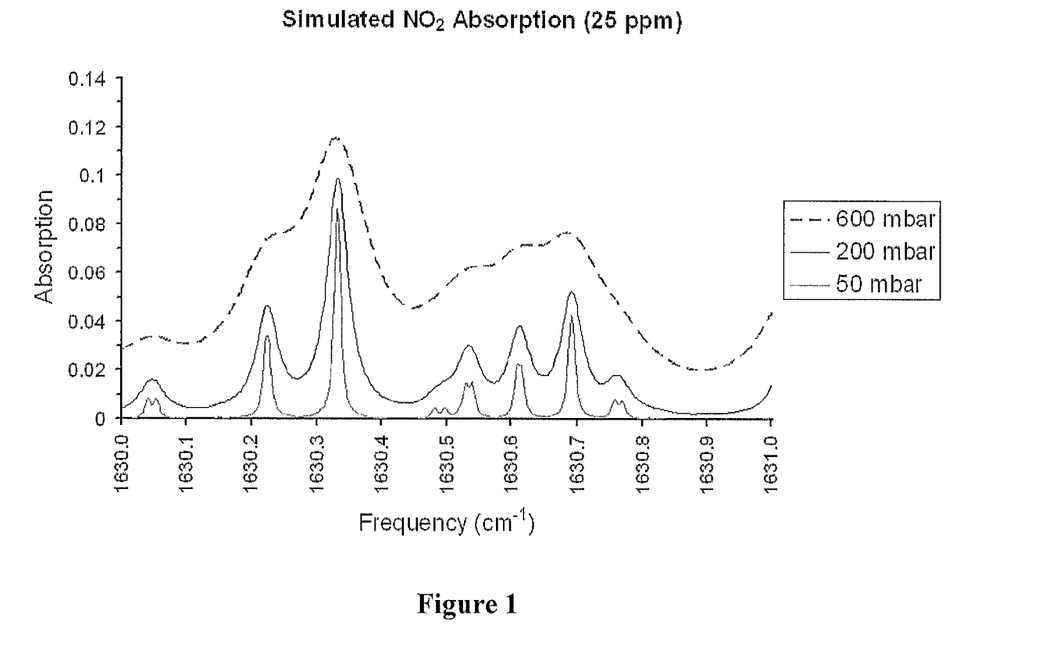
FIG. 1 which shows a simulated $NO_2$ absorption spectrum for 25 ppm sample at pressures of 50 mbar, 200 mbar and 600 mbar.

Using a line's amplitude to detect a species, however, neglects the width of the line and as a result gives the same intensity for both broad and narrow lines with the same amplitude (see Hollas). This can be seen in FIG. 1 which shows a simulated $NO_2$ absorption spectrum for a 25 ppm sample at pressures of 50 mbar, 200 mbar and 600 mbar (the simulation was generated using the HITRAN database of Rothman et al. and the SPECTRA software developed by Mikhailenko, et al., "Information-calculating system Spectroscopy of Atmospheric Gases. The structure and main functions," *Atmos. Oceanic Opt.* 18, 685-695 (2005). The low pressure data are helpful to resolve closely spaced lines. Even though the 600 mbar spectrum represents the contribution of about twelve times more molecules than the 50 mbar spectrum, it shows only about a 25% enhancement in peak absorption: The majority of additional absorption manifests itself in the broadening of the lines. It is important to note, however, that due to the closely spaced and complex nature of the $NO_2$ spectrum, the individual absorption features seen in the 50 mbar trace are not individual absorption lines, but instead are composed of closely spaced doublets or multiplets. For example, the absorption feature seen at 1630.23 $cm^{-1}$ is actually comprised of two lines separated by 0.004 $cm^{-1}$ resulting from the transitions between the (0 0 1)-(18 2 17) and (0 0 0)-(17 2 16) levels (note that the ($\nu_1$ $\nu_3$ $\nu_3$)-(N $K_a$ $K_c$) level notation is used), see Rothman et al. Even though the different rotational-vibrational transitions are not resolved, the absorption features that comprise several transitions can be employed for the estimation of trace species.

SUMMARY OF THE INVENTION

The present invention is directed to improving the accuracy of the detection of trace gases by directing a laser beam through a medium of interest and integrating across multiple absorption lines of the species (which can be recorded) by tuning the laser beam over a frequency range of interest.

When dealing with broadened lines, a more accurate measure of the absorption intensity can be achieved by integrating over the absorption line. Assuming that the absorbance $a=\sigma(v)LN$ is small (as is typically the case with trace gas detection), the integrated absorption may be written as:

$$S=\int \sigma(\sigma)NLdv \qquad (2)$$

If the separation between neighboring lines is much greater than the linewidth, the result of this integral may be used to obtain the actual concentration of the species in the cell. If, on the other hand, the lines are closely spaced such that the observed spectra are the result of many overlapping lines, the direct retrieval of the concentration using Eq. (2) may not be practical.

The intensity of each of the rotational-vibrational transitions depends on a number of factors such as the Einstein coefficients, energies of the transitions, etc. However in the low concentration limit, the sum of the areas of a set of absorption lines varies linearly with the concentration. This sum $S_T$ is defined as a new test parameter and it can be measured for different concentrations of the target species. As a result, by using pre-calibrated reference mixtures of the desired gas, one can define an $S_T$ vs. concentration curve that characterizes a particular experimental apparatus (e.g., this would take into account the optical path length L, the tuning range and other equipment-related factors). One could then identify the unknown concentrations of the species by recording their $S_T$ and identifying their corresponding positions on this chart.

This procedure enhances the sensitivity of detection in two ways. The first enhancement is due to the summing of the area under many spectral lines (which would boost the magnitude of the recorded signal). The second enhancement is from the fact that the integration has the effect of averaging the random components of the noise. Due to the fact that this data is acquired in a single scan (which can take 1 second or less), this effective averaging of the noise occurs in a much shorter time span than would be the case for averaging the signal by adding repeated scans. The sensitivity is further enhanced over standard laser absorption techniques in that one is not limited to working in the low-pressure regime (i.e., there is no need to resolve the lines individually). One need only work in a pressure regime that is appropriate to identify the spectra of the species unambiguously. This procedure is particularly valuable for molecules which have a large number of transitions grouped together.

Thus, the present invention is a new technique for the detection of trace species with high sensitivity and specificity. This new technique, which can be called Multiple Line Integrated Absorption Spectroscopy ("MLIAS"), uses a laser that can be tuned over many absorption features specific to the trace species (or their overtones) of interest. Integrated absorption data are used for the sensitivity measurements instead of a single feature traditionally employed in these measurements. Employing several absorption features (or the rotational-vibrational transitions), as many as hundreds of them in favorable cases, enhances the sensitivity of detection by several orders of magnitude. This technique can be employed for the detection of trace molecular species, explosive compounds, steroids and drugs using tunable lasers, such as diode lasers and quantum cascade lasers with or without external cavity, optical parametric oscillators, ion, solid state, and dye lasers. The power of this method is demonstrated by recording the absorption spectra of $NO_2$ across the R-branch and by integrating the resulting spectra. This resulted in a detection sensitivity of $NO_2$ that was improved by a factor of 15 compared to the sensitivity achieved using single line laser absorption spectroscopy with the same apparatus. The present invention offers much shorter data acquisition times for the real-time monitoring of trace gas species compared to the commonly employed procedure of adding repeated scans of the spectra to improve the signal-to-noise ratio.

BRIEF DESCRIPTION OF THE DRAWINGS

The foregoing and other features of the present invention will be more readily apparent from the following detailed description and drawings of an illustrative embodiment of the invention in which.

DESCRIPTION OF AN ILLUSTRATIVE EMBODIMENT OF THE INVENTION

Absorption spectroscopy of $NO_2$ is carried out using a short-path (12.5 cm) absorption cell 10 filled with different concentrations of $NO_2$ (25 ppm, 5 ppm, 2.5 ppm, 1 ppm, 0.5 ppm and 0.25 ppm). The cell 10 may be a single pass absorption cell, a simple multipass cell, a multipass absorption cell (e.g., Herriott cell, astigmatic cell); cavity ringdown spectroscopy cell; Off-axis integrated cavity output spectroscopy cell and the variants there off.

Figure 2:
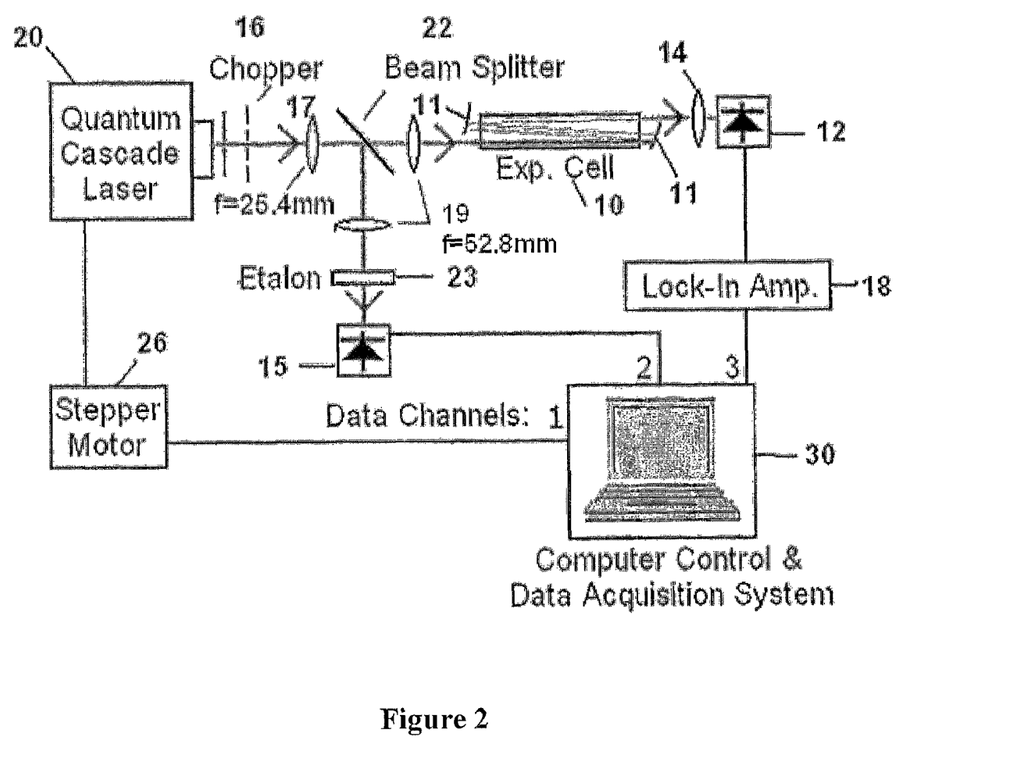
FIG. 2 is a block diagram of the sensor of the present invention.

The schematic of the arrangement of apparatus used for absorption spectroscopy of $NO_2$ is shown in FIG. 2. FIG. 2 shows a Quantum Cascade laser 20 whose continuous output is chopped into laser pulses by a mechanical chopper 16 running at 3.9 kHz. The laser pulses pass through a first lens 17 of a beam expander and are then incident on a beam splitter 22. One part of the beam is reflected downwardly in the drawing to the second lens 19 of the beam expander. The other part of the beam travels through the beam splitter and enters cell 10. Two, rectangular, flat, protected gold mirrors 11 are aligned to reflect the beam back and forth seven times through the cell creating a multi-pass cell that increased the pathlength to 0.88 m. Upon leaving the cell the laser pulse passes through a lens 14 and enters a photodetector 12. The photodetector may be a two-stage, TB-cooled, IR photovoltaic detector (e.g., the PVI-2TE-8 manufactured by Vigo), which can be operated in a room-temperature environment. The detectors are optically immersed in a high refractive index, hyperhemispherical lens that is part of the detector package.

The output of detector 12 is applied to a Lock-In amplifier 18 for phase sensitive detection, i.e., it detects signals at the chopper frequency or its harmonics to improve the signal-to-noise ratio. The lock-in amplifier 18 may be e.g., a Stanford Research Systems SR830 DSP with the time constant set to 1 ms. The output of the Lock-in amplifier is applied to input 3 of a data acquisition board and computer control 30, where the signal is measured. In the other beam path, which is called the reference beam path, the laser pulse exiting the beam expander lens 19 is applied to an Etalon 23, which matches the etaloning effect of the cell 10. The laser beam that passes through the Etalon 23 is picked up by photodetector 15 as a reference signal and is applied to input 2 of the data acquisition board 30. In acquisition board 30 the absorption signal from the laser pulse that bounced back and forth in the cell 10 has the reference signal subtracted from it and the result is stored in the computer as one set of data to be summed to arrive at the final result. Because Etalon 23 and cell 10 have similar etaloning effects, the subtraction essentially cancels the etaloning effect in the system.

The stepper motor 26 rotates the external cavity grating of the laser 20 to tune the laser to a new frequency. Then the process is repeated at the new frequency to cover the tuning range of interest. The sum of the difference signals calculated by computer 30 is directly proportional to the amount of trace gas species in the sample. The great accuracy of the present invention is achieved by extending the path length with the multi-pass cell 10 and then summing the absorption spectra over many transitions by tuning the laser over a frequency range covering the transitions of interest.

The $NO_2$ mixtures were prepared by loading the cell 10 with a pre-calibrated mixture of $NO_2$ in Zero Air (a mix of 20.9% $O_2$ and 79.1% $N_2$). The $NO_2$ mixtures were at concentrations of 25 ppm and 5 ppm and were certified by Gasco Affiliates, LLC to ±10% of the specified concentration. Other concentrations were created by loading the cell with the 5 ppm mixture to a certain pressure, and then adding Zero Air to increase the pressure to the desired final value. For example, the 1 ppm concentration was generated by first loading the cell with 120±10 mbar of the pre-calibrated 5 ppm mix of $NO_2$ before additional Zero Air was added to reach a final pressure of 600±30 mbar. Due to limitations in the accuracy of the vacuum/mixing apparatus, the concentrations prepared are believed to be accurate to ±30% (e.g., the 2.5 ppm concentration mixture is believed to contain between 1.75 and 3.25 ppm $NO_2$), For lower concentrations, the uncertainty rises to ±40% for 0.5 ppm and 0.25 ppm. The mixing apparatus was tested by generating several concentrations of $NO_2$, and comparing the recorded absorption line intensities with the calculated intensities based on HITRAN data base of the Rothman et al. article, which is incorporated herein in its entirety. This confirmed that the mixtures were within the expected uncertainty.

Experiments in the mid and far-infrared range typically suffer from significant etalon effects, i.e., interference between the multiple reflections of the laser beam between two reflecting surfaces. Etalonning was identified in the signal generated by the present invention due to beam splitter 22. The etalon effects from the beam splitter were removed by placing it between the lenses 17, 19 of the 2×beam expander ($f_1$=25.4 mm, $f_2$=52.8 mm); the short focal lengths were necessary to create enough divergence to remove the etalon peaks. Wedge windows (AR coated ZnSe with faces that were 1° away from parallel) were used in the cell 10 to remove etalonning that occurs with standard, parallel faced windows.

The quantum cascade laser 20 itself exhibited etalonning due to its anti-reflection coatings. This was compensated by subtracting empty-cell scans of the laser (which characterized the tuning characteristics of the laser including etalonning) from scans of the cell loaded with $NO_2$, The reference signal from detector 15 after the reference beam passes through Etalon 23 is thus subtracted from the signal from the detector 12 and the subtraction occurs in data acquisition board 30, which may be a National Instruments Data Acquisition Board PCI-6040E.

A suitable Quantum Cascade Laser source 20 can be purchased from Daylight Solutions (Model TLS-CW-MHF) and has a tuning range of 1601.3 $cm^{-1}$ to 1670 $cm^{-1}$. The external cavity is of the Littrow configuration which allows a wide range of mode hop-free tuning, provides a narrow line width (~0.001 $cm^{-1}$), and is thus well suited for spectroscopic measurements. The laser tuning is monitored using Etalon 23 and the display screen of the controller of laser 20 (not shown in FIG. 2), as well as by comparing recorded spectra with line positions identified in the HITRAN database.

The laser power varies as a function of tuning, with a minimum output power of 14 mW at 1601.3 $cm^{-1}$, and a maximum of 21 mW at 1640.4 $cm^{-1}$. The output power at 1630 $cm^{-1}$ (the frequency selected for the laser absorption spectroscopy) was 19.5 mW. Broad range tuning is achieved entirely by rotating the external cavity grating via stepper motor 26; no current or temperature tuning was necessary. The system may be set to one of six pre-set tuning rates possible with the stepper motor, the slowest of which was 3.125 $cm^{-1}$/sec (the tuning rate used in recording $NO_2$ absorption spectra). The minimum spot size of the beam is approximately 2 mm.

Figure 3A:
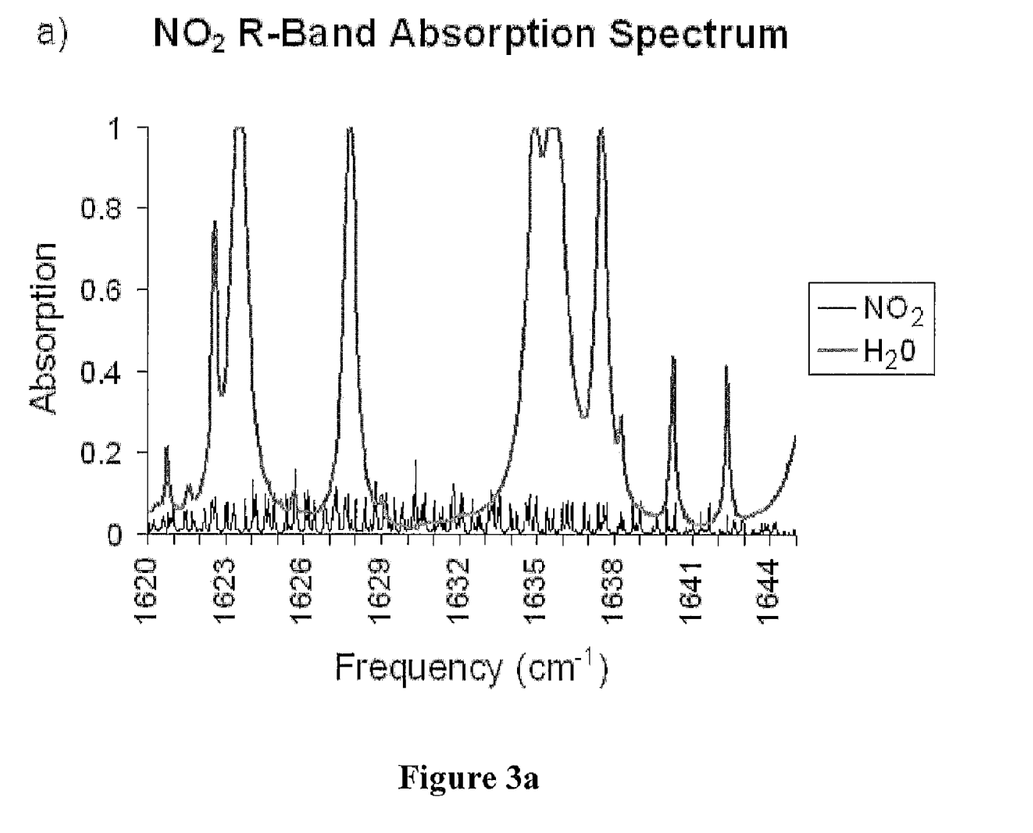
FIG. 3a shows a simulated spectrum illustrating the regions where the water lines overlap with $NO_2$ lines.
Figure 3B:
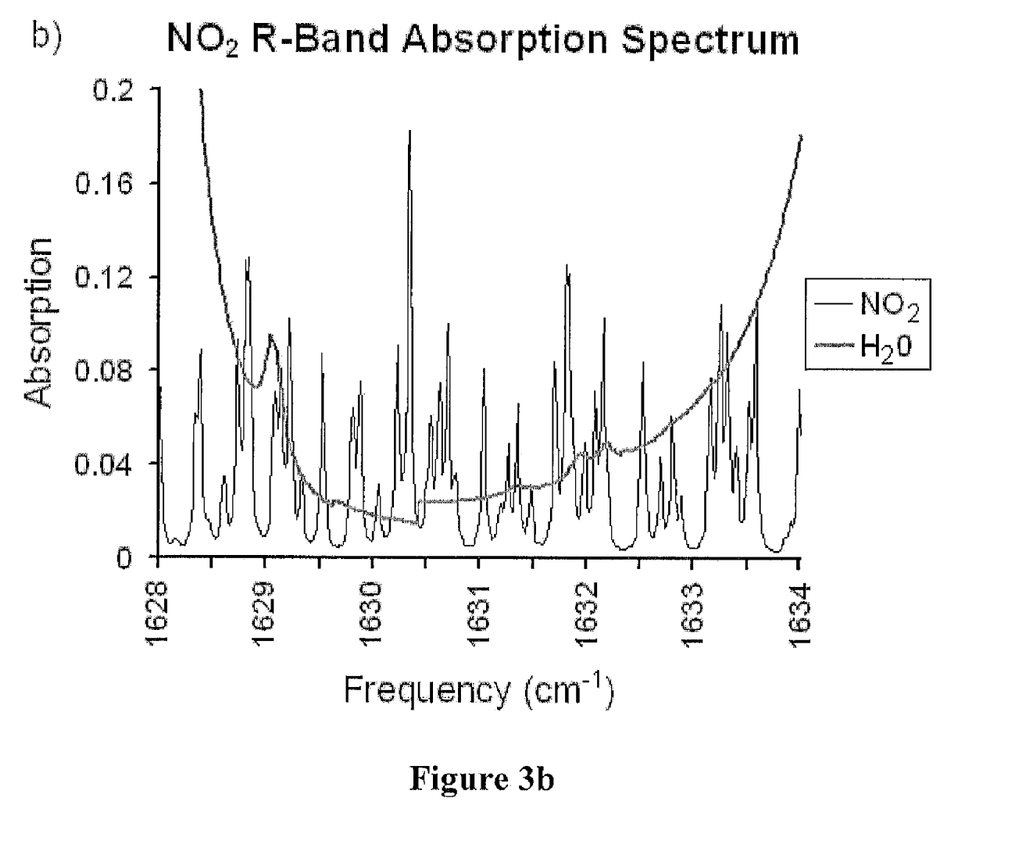
FIG. 3b is a close-up of the region shown in FIG. 3a where the spectrum is recorded and integrated.

In order to integrate the recorded spectra for multiple lines over a desired range of frequencies, the laser source must tune without mode hops across that range. The quantum cascade laser used must be capable of mode hop-free tuning between 1603.5 $cm^{-1}$ and 1670 $cm^{-1}$. This provides access to half of the $NO_2$ P-branch and the entire $NO_2$ R-branch (the peak absorption in the R-branch occurs at 1630.3 $cm^{-1}$). The next consideration is to select a region with a strong dense spectrum, and free from interference due to water lines. FIG. 3a shows a simulated $NO_2$ spectrum illustrating the regions where the water lines (due to ambient water vapor in the beam path leading to the cell 10) overlap and thus overwhelm any potential signal from the $NO_2$ R-branch. FIG. 3a shows simulated $NO_2$ spectrum at 50 ppm at 200 mbar for the R-branch between 1620 $cm^{-1}$ and 1645 $cm^{-1}$. Overlaid on the spectrum are the water lines. This spectrum was used to select a region with a strong dense $NO_2$ spectrum that was free from interference due to water lines. As described before, this simulation was generated using the HITRAN database and the SPECTRA software developed by Mikhailenko, et al., which is incorporated herein in its entirety. The strength of the water lines was selected to match typical conditions in the mid-latitude U.S. during the summer months (the water vapor density used was 14.97 $g/m^3$ which corresponds to a relative humidity of 71% at 23° C., and is the average humidity in Washington D.C. in July). As seen from FIG. 3a, the region between the water lines at 1627.82 $cm^{-1}$ and 1634.97 $cm^1$ proves to be the longest continuous region in which absorption due to the water lines does not overwhelm the $NO_2$ lines, and covers the peak of the R-branch. Due to the broad width of these water lines, the ability to record $NO_2$ spectra was limited to the region between 1628.8 $cm^{-1}$ and 1634.5 $cm^{-1}$. It is important to note that this tuning range covered over 500 $NO_2$ transitions, of which approximately 20% may be considered relatively strong (i.e., having transition strengths over 10% that of the strongest transition in the R-branch). It should also be noted that the strength and width of the waterlines in the simulation were calibrated to match the apparatus of FIG. 2 (which has a 1 meter path from the laser to the cell).

To facilitate the analysis, the $NO_2$ concentrations were maintained at a pressure of 600±30 mbar. This narrowed the line width enough so that it was possible to determine the frequency at which the interference from the water lines prevented the accurate recording of $NO_2$ spectra. The data were recorded by reading the output from Vigo detectors 12, 15 into computer 30 using a National Instruments (model PCI-6040E) data acquisition board. A virtual instrument constructed using LabView for Windows is used to record the data.

Absorption spectra were recorded for several concentrations of $NO_2$: 25 ppm, 12.5 ppm, 5 ppm, 2.5 ppm, 1 ppm, 0.5 ppm, 0.25 ppm and 0 ppm. The 0 ppm spectrum was recorded to determine the noise contributions from all components of the system as well as the contributions from the tails of the water lines in the region of interest, and was generated by filling the sample cell with Zero Air. It should be stated that high-end estimates for the errors and uncertainties were used and therefore the improvement in the sensitivity of detection employing multiple line integrated absorption spectroscopy set forth herein is a conservative estimate.

Figure 4:
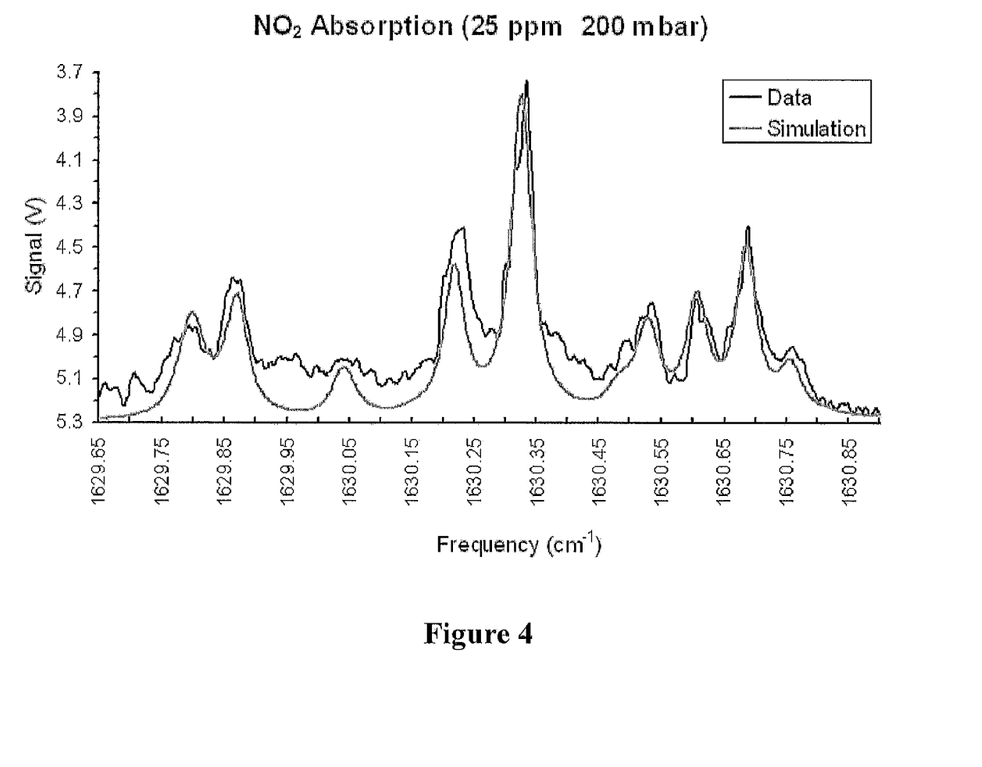
FIG. 4 is a graph of the absorption spectrum of $NO_2$ recorded from 1629.65 to 1630.33 $cm^{-1}$.

The sensitivity of the apparatus using laser absorption spectroscopy was determined by recording $NO_2$ spectra at concentrations of 25 ppm, 12.5 ppm and 5 ppm (at a pressure of 200±20 mbar) between 1629.65 $cm^{-1}$ and 1630.95 $cm^{-1}$ FIG. 4 shows the spectrum recorded at a concentration of 25 ppm (concentration=25±3 ppm, pressure=200±20 mbar). The strong absorption feature located at approximately 1630.33 $cm^{-1}$ was used to determine the sensitivity of the apparatus. This feature is comprised of two strong, closely spaced doublets (identified in Table 1). The gray trace is the simulated spectrum based on HITRAN data.

Figure 5:
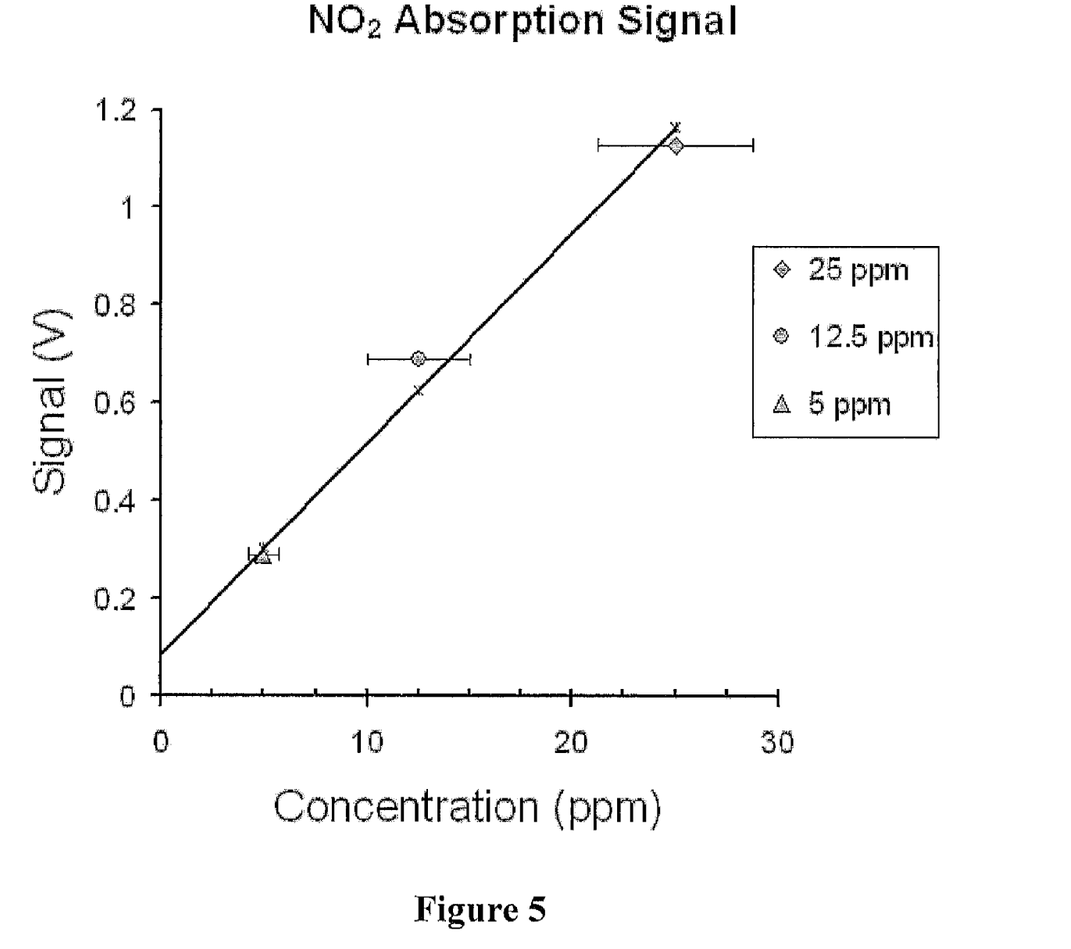
FIG. 5 is a graph of absorption signal intensity of $NO_2$ versus various concentrations.

The pressure was chosen to facilitate the identification and measurement of individual absorption features. The range was chosen because it allows the analysis of the strongest absorption feature in the R-branch. This feature is located at approximately 1630.33 $cm^{-1}$ and is in fact comprised of two, closely spaced doublets. All four lines are grouped within 0.003 $cm^{-1}$. This is narrower than the 0.04 $cm^{-1}$ FWHM of the individual lines at 200 mbar, and results in the single observed absorption feature. The two doublets that form the feature are identified in table 1. The observed amplitude of this absorption feature is plotted for each concentration in FIG. 5. FIG. 5 shows the absorption signal intensity of $NO_2$ recorded at concentrations of 25 ppm, 12.5 ppm and 5 ppm. The y-intercept of the weighted least squares fit of the data indicates the sensitivity of the apparatus. In particular, a weighted linear least squares fit of the data is used to determine the sensitivity. The y-intercept value of 0.078 V is divided by the slope of the fit (0.0432 V/ppm) to obtain a sensitivity of approximately 1.8 ppm.

TABLE 1

| Central Frequency of Doublet ($cm^{-1}$) | Upper State $(v_1 v_3 v_3)$-$(N' K'_a K'_c)$ | Lower State $(v_1 v_3 v_3)$-$(N'' K''_a K''_c)$ |
|---|---|---|
| 1630.326 | (0 0 1)-(17 1 16) | (0 0 0)-(16 1 15) |
| 1630.328 | (0 0 1)-(17 0 17) | (0 0 0)-(16 0 16) |

In Table 1 the data are tabulated for the Spectral Line parameters from HITRAN for the major $NO_2$ doublets in the R-branch that make up the absorption feature at 1630.33 $cm^{-1}$ seen in FIG. 4.

Figure 6:
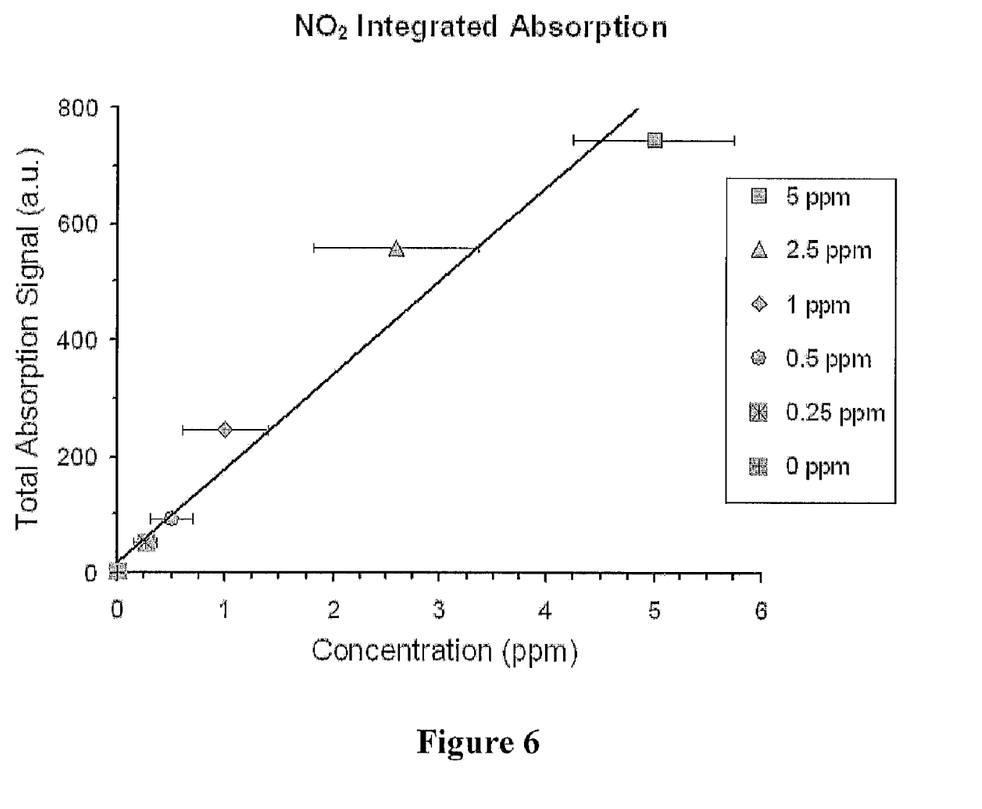
FIG. 6 is a graph of total absorption versus concentration.

To measure the sensitivity that may be obtained by integrating the multi-line absorption spectra recorded over a tuning range, the absorption spectra were recorded for six concentrations of $NO_2$ (5 ppm, 2.5 ppm, 1 ppm, 0.5 ppm, 0.25 ppm and 0 ppm), at a pressure of 600±30 mbar, The spectra were recorded in the frequency range 1628.8 $cm^{-1}$ to 1634.5 $cm^{-1}$. These concentrations were selected to ensure that the data were in the weakly absorbing regime (i.e., the absorption of the strongest line was less than 5%). The data from each spectrum were then integrated to yield the total absorption strength $S_T$ for the corresponding concentration. Each of these values was subtracted from the total absorption strength recorded for the 0 ppm concentration; this resulted in the area under the recorded absorption spectrum for the corresponding concentration ("the total absorption signal for a given concentration"). FIG. 6 shows a plot of the total absorption signal vs, concentration, as well as a weighted linear least-squares fit of this data (the y-axis is given in arbitrary units). The expected linear relationship between the integrated absorption signals of the various concentrations is seen. The y-intercept is used to determine the sensitivity of detection.

The instrument's sensitivity is determined from the y-intercept of the linear fit. The y-intercept value of 18.7 for the total absorption units is divided by the slope of the fit (161 total absorption units/ppm) to obtain a sensitivity of approximately 120 ppb. This shows a factor of 15 improvement in sensitivity compared to single line laser absorption spectroscopy conducted using the same apparatus. It should be noted that even though the $NO_2$ mixtures were generated using Zero-Air (a dehumidified air mixture); the results are representative of what one would expect if the $NO_2$ was in ambient air. This is a result of the layout, where the laser beam travels through approximately 1 meter of ambient air before reaching the cell whose effective path-length is 88 cm.

The present invention is a technique which enhances the sensitivity of a spectrometer for trace gas detection by integrating the absorption spectra from multiple spectral lines. In particular, laser absorption spectroscopy is performed with a tunable, CW quantum cascade laser, and a short-path absorption cell to detect low concentrations of $NO_2$ with a sensitivity of approximately 1.8 ppm. Employing the multiple line integrated absorption technique with the same apparatus can detect concentrations of $NO_2$ with a sensitivity on the order of 120 ppb, demonstrating a greater than 1 order of magnitude improvement in the instrument's sensitivity.

This technique can be applied to improve the sensitivity of detection of trace gases in general, including traces of chemical compounds used in the explosive devices. This technique will be able to provide very significant improvement in the sensitivity of detection particularly for polyatomic species such as $NO_2$ that have dense rotational-vibrational spectra over a relatively compact frequency range. Though this embodiment was described using an external cavity tunable quantum cascade laser with a wide mode hop-free tuning range, the technique of the present invention could be applied using any tunable laser source that is capable of tuning across multiple transitions of the target species. Additional improvements to the sensitivity may be achieved by using this technique with long optical path-length apparatus such as a Herriott cell or ICOS, and should enable sub-parts per billion sensitivity.

While the invention has been particularly shown and described with reference to a preferred embodiment thereof, it will be understood by those skilled in the art that various changes in form and details may be made therein without departing from the spirit and scope of the invention.

I claim:

1. A method for detecting trace gases using absorption spectroscopy, comprising the steps of:
   directing a laser beam that can be tuned over a frequency range covering at least four absorption lines or features of the target species through a medium containing the trace gas;
   detecting the laser beam after it passes through the medium so as to generate a spectral signal;
   recording the detected spectral signal;
   changing the laser frequency to a new frequency in the frequency range;
   repeating the detecting and recording steps at the new laser frequency; and
   integrating the recorded spectra for at least four absorption lines or features over the frequency range by summing the detected spectral signals for said absorption lines or features at each frequency of the frequency range.

2. The method of claim 1 wherein the step of changing the laser frequency is achieved by tuning an external cavity grating with a stepper motor.

3. The method of claim 1 wherein the step of changing the laser frequency is achieved by changing an injection current of the laser.

4. The method of claim 1 wherein the gas being detected is $NO_2$.

5. The method of claim 1 further including the steps of:
   splitting the laser beam so that part of the laser beam enters the medium of interest and part is reflected to a second detector;
   detecting the laser beam at the second detector as a reference signal and recording the reference signal information;
   subtracting the recorded reference signal from the recorded spectral signal to get a difference signal; and
   integrating the difference signals over the frequency range by summing the difference signals at each frequency of the frequency range to yield total absorption strength.

6. The method of claim 5 further including the steps of providing an etalon between the beam splitter and the second detector which has etaloning effects similar to the cell so that upon subtracting the recorded reference signal from the recorded absorption cell signal the etaloning effects of the system are compensated.

7. The method of claim 1 wherein the laser beam is a pulsed beam and the generation of the pulsed laser beam involves the steps of:
   creating a continuous wave laser beam; and
   using a mechanical chopper located at the laser output to change the continuous wave laser output to a series of laser pulses.

8. The method of claim 7 wherein the laser beams are detected by phase-sensitive detection using a lock-in amplifier and the lock-in amplifier is phase locked to the frequency of the generated laser pulses.

9. The method of claim 1 wherein the laser beam is a pulsed beam generated by a pulsed laser.

10. The method of claim 1 wherein the target species is in an enclosed cell and further including the step of providing mirrors on the input and output of the cell arranged so that the beam is reflected back and forth through the cell to form a multi-pass cell.

11. The method of claim 1 wherein the target species is in an enclosed cell that is one of a single pass absorption cell, a simple multipass cell, multipass absorption cells (e.g., Herriott cell, astigmatic cell); cavity ringdown spectroscopy cell; and Off-axis integrated cavity output spectroscopy cell.

12. The method of claim 1 wherein the step of integrating involves summing the recorded spectra of multiple absorption lines or features in excess of four.

13. The apparatus of claim 12 where in the trace gas is NO2 and the step of integrating involves summing the recorded spectra over several hundred absorption lines or features.

14. Apparatus for detecting trace gases using absorption spectroscopy, comprising:
   a medium in which the trace gas is located;
   a tunable external cavity quantum cascade laser source that provides a laser output covering at least four absorption lines or features of the trace species, said laser output being directed into said medium;
   a photodetector for detecting the laser beam after it emerges from the medium and generating spectral detection signals related thereto;
   a storage medium for storing the spectral detection signals from the photodetector,
   a tuner for tuning the laser over a frequency range of interest; and
   an integrator for summing the stored spectral detection signals for at least four lines at each frequency of the range of frequencies.

15. The apparatus of claim 14 wherein the trace gas is $NO_2$.

16. The apparatus of claim 14 wherein the frequency range of interest corresponds to a wave number range from 1601.3 $cm^{-1}$ to 1670 $cm^{-1}$.

17. The apparatus of claim 14 wherein the tunable laser source is a source of a pulsed laser beam formed from the output of a continuous wave laser and a mechanical chopper that chops the continuous wave laser output into pulses.

18. The apparatus of claim 17 further including a lock-in amplifier between the photodetector and the storage medium operated so that phase lock-in detection at the chopper frequency or its harmonics is possible, thus improving signal-to-noise ratio of the detection.

19. The apparatus of claim 17 wherein the chopper is operated at a rate of 3.9 kHz.

20. The apparatus of claim 14 wherein a mechanical beam chopper is employed to produce a pulsed laser beam from a continuous laser source.

21. The apparatus of claim 14 wherein the tuner is a stepper motor connected to an external cavity grating which forms part of the external cavity quantum cascade laser source to change the output frequency of the laser.

22. The apparatus of claim 14 further comprising:
   a beam splitter intercepting a portion of the laser beam before it enters the medium and reflecting part of it in a different direction;
   a second photodetector intercepting the laser beam reflected by the beam splitter and generating a signal related thereto that serves as a reference signal to compensate for laser intensity fluctuations and etaloning effects;
   a storage device for storing the reference signals; and
   a subtraction circuit for subtracting the stored reference signals from the stored detection signals to form difference signals; and wherein the integrator sums the difference signals at each frequency of the frequency range yielding the total absorption strength.

23. The apparatus of claim 22 further comprising an Etalon located between the beam splitter and the second photodetector to compensate for etaloning effects in the system.

24. The apparatus of claim 22 further comprising a beam expander including at least two lenses incorporated before the medium and in the reference beam.

25. The apparatus of claim 14 wherein the medium is in an enclosed cell and further including mirrors on the input and output of the cell arranged so that the beam is reflected back and forth through the cell to form a multi-pass cell.

26. The apparatus of claim 25 wherein the enclosed cell is one of a single pass absorption cell, a simple multipass cell, a multipass absorption cell (Herriott cell, astigmatic cell); cavity ringdown spectroscopy cell; and an Off-axis integrated cavity output spectroscopy cell.

27. The apparatus of claim 14 wherein the trace gases are in the atmosphere and are one of automobile emissions, industrial emissions, and explosive compounds.

28. The apparatus of claim 14 wherein the laser is one of semi-conductor lasers (diode lasers and quantum cascade lasers), optical parametric oscillators, tunable dye and solid state lasers.

29. The apparatus of claim 14 wherein the tuner is a circuit capable of changing an injection current directed into the laser.

30. The apparatus of claim 14 wherein the integrator sums the stored detected signals for multiple absorption lines in excess of four.

31. The apparatus of claim 30 where in the trace gas is NO2 and the integrator sums the stored spectra over several hundred absorption lines or features.

* * * * *